United States Patent [19]
Fürstenwerth

[11] Patent Number: 4,892,958
[45] Date of Patent: Jan. 9, 1990

[54] PREPARATION OF 5-AMINO-1-PHENYL-4-NITROPYRAZOLES

[75] Inventor: Hauke Fürstenwerth, Leverkusen, Fed. Rep. of Germany

[73] Assignee: Bayer Aktiengesellschaft, Leverkusen, Fed. Rep. of Germany

[21] Appl. No.: 282,225

[22] Filed: Dec. 8, 1988

[30] Foreign Application Priority Data

Dec. 17, 1987 [DE] Fed. Rep. of Germany ........ 3742819

[51] Int. Cl.$^4$ ............................................. C07D 231/16
[52] U.S. Cl. ................................................ 548/362
[58] Field of Search ....................................... 548/362

[56] References Cited

U.S. PATENT DOCUMENTS 3,285,930 11/1966 Williams ............................... 548/206
4,685,956 8/1987 Gehring et al. ...................... 348/362

*Primary Examiner*—R. W. Ramsuer
*Attorney, Agent, or Firm*—Sprung Horn Kramer & Woods

[57] ABSTRACT

A process for the preparation of a 5-amino-1-phenyl-4-nitropyrazole of the formula

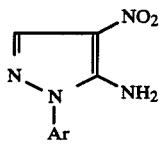

(I)

in which
  Ar is optionally substituted phenyl, which comprises reacting an arylhydrazine of the formula

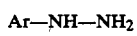

(II)

with 3-chloro-4-nitro-isothiazole of the formula

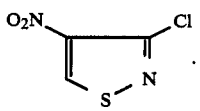

(III)

10 Claims, No Drawings

PREPARATION OF 5-AMINO-1-PHENYL-4-NITROPYRAZOLES

The invention relates to a new process for the preparation of 5-amino-1-phenyl-4-nitropyrazoles which are used as herbicides.

It has been disclosed that 5-amino-1-phenyl-4-nitropyrazoles can be obtained when arylhydrazines are initially cyclized with 2-chloroacrylonitrile, the resulting 5-amino-1-phenyl-pyrazoles are, in a second step, acylated on the amino group, the resulting compounds are then, in a third step, nitrated and, in a fourth step, the acyl protective group on the amino function in the 5-position of the pyrazole ring is eventually removed (cf., for example, EP-A 154,115 or EP-A 224,831).

The disadvantage of the previously known process is the multi-step reaction procedure which must be considered as uneconomical regarding expense and yield.

It has now been found that 5-amino-1-phenyl-4-nitropyrazoles of the general formula (I)

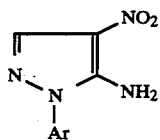

in which

Ar stands for optionally substituted phenyl, are obtained when arylhydrazines of the formula (II)

in which

Ar has the abovementioned meaning, are reacted with 3-chloro-4-nitro-isothiazole of the formula (III)

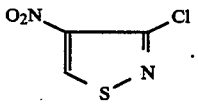

if appropriate in the presence of an auxiliary base, if appropriate in the presence of a diluent and if appropriate in the presence of a reaction auxiliary.

Here, it should be considered as extremely surprising that the arylhydrazines of the formula (II) react with the 3-chloro-4-nitro-isothiazole of the formula (III) in such a smooth way since due to the polyfunctionality of the starting compounds employed and of the final products of the formula (I), the occurrence of a large number of side-reactions was rather to be expected. The fact that the sulphur from the isothiazole ring, said sulphur being liberated as a by-product, did not cause side-reactions or purification problems was also unexpected. This is the first and only case, in the known literature, of the direct conversion of an isothiazole compound to a pyrazole derivative.

Compared with the previously known multi-step preparation process, the process according to the invention exhibits a number of advantages. Thus, the desired final products of the formula (I) are obtained in high yields and in a purity which is so high that additional complicated purification operations can generally be dispensed with. A further advantage is that the single-step reaction procedure leads to considerable savings of expensive starting materials, auxiliaries and amounts of energy and waste water, which is a considerable improvement compared with the prior art, not only from the economic but also from the ecological point of view.

Formula (I) provides a general definition of the 5-amino-1-phenyl-4-nitropyrazoles which can be prepared with the aid of the process according to the invention. Compounds of the formula (I) which can preferably be prepared are those in which Ar stands for phenyl which is optionally monosubstituted or polysubstituted by identical or different substituents, suitable substituents in each case being: cyano, nitro, halogen, in each case straight-chain or branched alkyl, alkoxy or alkoxycarbonyl, each having 1 to 4 carbon atoms, in each case straight-chain or branched halogenoalkyl or halogenoalkoxy, each having 1 to 4 carbon atoms and 1 to 9 identical or different halogen atoms, or a radical $-S(O)_n-R^3$, where $R^3$ stands for amino and for in each case straight-chain or branched alkyl, alkylamino, dialkylamino or halogenoalkyl, each having 1 to 4 carbon atoms in the individual alkyl moieties and in the case of halogenoalkyl, having 1 to 9 identical or different halogen atoms, and n stands for a number 0, 1 or 2.

Compounds of the formula (I) which can particularly preferably be prepared are those in which Ar stands for phenyl which is optionally monosubstituted to pentasubstituted by identical or different substituents, suitable substituents in each case being: cyano, nitro, fluorine, chlorine, bromine, iodine, methyl, ethyl, n- or i-propyl, n-, i-, s- or t-butyl, methoxy, ethoxy, methoxycarbonyl, ethoxycarbonyl, trifluoromethyl, trichloromethyl, dichlorofluoromethyl, difluorochloromethyl, chloromethyl, dichloromethyl, difluoromethyl, pentafluoroethyl, tetrafluoroethyl, trifluorochloroethyl, trifluoroethyl, difluorodichloroethyl, trifluorodichloroethyl, pentachloroethyl, trifluoromethoxy, trichloromethoxy, dichlorofluoromethoxy, difluorochloromethoxy, chloromethoxy, dichloromethoxy, difluoromethoxy, pentafluoroethoxy, tetrafluoroethoxy, trifluorochloroethoxy, trifluoroethoxy, difluorodichloroethoxy, trifluorodichloroethoxy, pentachloroethoxy or a radical $-S(O)_n-R^3$, where $R^3$ stands for amino, methylamino, ethylamino, dimethylamino, diethylamino, fluorodichloromethyl, difluoromethyl, tetrafluoroethyl, trifluorochloroethyl, trichloromethyl, trichloroethyl, trifluoromethyl, methyl or ethyl, and n stands for a number 0, 1 or 2.

Compounds of the formula (I) which can very particularly preferably be prepared are those in which Ar stands for phenyl which is optionally monosubstituted to pentasubstituted by identical or different substituents, suitable substituents being: fluorine, chlorine, bromine, methyl, ethyl, methoxy, ethoxy, trifluoromethyl, trifluoromethoxy, trifluoromethylthio, trifluoromethylsulphinyl or trifluoromethylsulphonyl.

If, for example, 2,6-dichloro-4-trifluoromethylphenylhydrazine and 3-chloro-4-nitro-isothiazole are used as starting substances, the course of the reaction of the process according to the invention can be represented by the following equation:

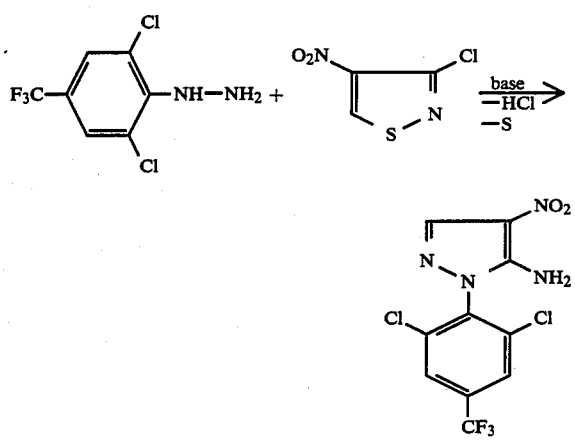

Formula (II) provides a general definition of the aryl-hydrazines required as starting substances for carrying out the process according to the invention. In this formula (II), Ar preferably stands for those radicals which have already been mentioned in connection with the description of the substances of the formula (I) obtainable according to the invention as being preferred for these substituents.

The arylhydrazines of the formula (II) are known or can be obtained in analogy to known processes (cf., for example, EP-A 154,115 or EP-A 224,831 or EP-A 187,285 or EP-A 34,945).

The 3-chloro-4-nitro-isothiazole of the formula (III) furthermore required as starting compound for carrying out the process according to the invention is also known (cf. U.S. Pat. No. 3,285,930).

The process according to the invention is preferably carried out in the presence of a suitable auxiliary base.

Suitable bases are, in particular, amines of the formula (IV)

in which $R^1$ and $R^2$ independently of one another each stand for hydrogen, alkyl, cycloalkyl or for in each case optionally substituted aralkyl, aryl or heteroaryl, or together with the nitrogen atom to which they are bonded stand for an optionally substituted heterocyclic ring which can, if appropriate, contain further hetero atoms.

Preferably used amines are those of the formula (IV) in which $R^1$ and $R^2$ independently of one another stand for hydrogen, straight-chain or branched alkyl having 1 to 4 carbon atoms, for cycloalkyl having 3 to 7 carbon atoms or for phenyl or benzyl, each optionally monosubstituted, disubstituted or trisubstituted by identical or different substituents, suitable substituents being: fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trifluoromethylthio, methoxycarbonyl or ethoxycarbonyl, or $R^1$ and $R^2$ together with the nitrogen atom to which they are bonded stand for a five- or six-membered saturated heterocyclic ring which can, if appropriate, contain 1 to 3 further identical or different hetero atoms, such as in particular nitrogen, oxygen or sulphur. $R^1$ and $R^2$ independently of one another stand particularly preferably for hydrogen, methyl, ethyl, n- or i-propyl, n-, i-, s- or t-butyl, cyclohexyl, phenyl or benzyl, or together with the nitrogen atom to which they are bonded stand for a 1-pyrrolidinyl radical, for a 1-piperidinyl radical or for a 4-morpholinyl radical.

The amines of the formula (IV) which are to be employed as auxiliary bases, if necessary, are generally known compounds of organic chemistry.

In addition, further inorganic or organic bases may be added as auxiliaries. Suitable auxiliaries are all customary inorganic or organic bases. These include, for example, alkali metal hydroxides or alkaline earth metal hydroxides, such as sodium hydroxide, potassium hydroxide, magnesium hydroxide or calcium hydroxide, alkali metal carbonates, alkali metal hydrogen carbonates or alkali metal acetates, such as sodium carbonate, potassium carbonate, sodium hydrogen carbonate or sodium acetate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU). The hydroxides, carbonates or hydrogen carbonates of alkali metals or alkaline earth metals are preferably used.

Suitable diluents for carrying out the process according to the invention are inert organic solvents or mixtures thereof with water. These include in particular aliphatic, alicyclic or aromatic hydrocarbons, optionally halogenated, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran, ethylene glycol dimethyl ether or ethylene glycol diethyl ether, ketones, such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate, carboxylic acids, such as acetic acid or propionic acid, alcohols, such as methanol, ethanol, propanol, butanol, ethylene glycol, its monomethyl or monoethyl ether, or their mixtures with water. Preferably, alcohols or their mixtures with water are used.

If amines in liquid form are used as auxiliary base, it is also possible to employ the former in suitable excess to act simultaneously as diluent.

If required, the process according to the invention can also be carried out in the presence of an acid reaction auxiliary. Suitable reaction auxiliaries are customary protonic acids or Lewis acids. Inorganic mineral acids such as hydrochloric acid or sulphuric acid, aliphatic or aromatic carboxylic or sulphonic acids, such as acetic acid, methanesulphonic acid or p-toluenesulphonic acid, Lewis acids, such as boron trifluoride, iron trichloride, aluminum trichloride or zinc dichloride or acid ion exchangers are preferably used. Hydrochloric acid or sulphuric acid are particularly preferably used.

When carrying out the process according to the invention, the reaction temperatures can be varied within a relatively wide range. In general, the process is carried out at temperatures between −30° C. and +150° C., preferably at temperatures between 20° C. and 100° C.

1.0 to 1.5 moles, preferably 1.0 to 1.3 moles, of 3-chloro-4-nitro-isothiazole of the formula (III) and if appropriate 1.0 to 10.0 moles, preferably 1.0 to 5.0 moles, of auxiliary base and if appropriate 1.0 to 20.0 moles, preferably 1.0 to 10.0 moles, of acid reaction auxiliary are generally employed per mole of arylhydrazine of the formula (II), to carry out the process according to the invention.

If amines of the formula (IV) are used as auxiliary base, they are initially reacted with the 3-chloro-4-nitroisothiazole of the formula (III), and the arylhydrazine of the formula (II) and the acid reaction auxiliary are then added to the reaction mixture thus obtainable. The reaction is carried out and the reaction products are worked up and isolated by generally customary methods, for example by removing the organic diluent, precipitating the reaction product in water, filtering off the product thus obtained with suction and drying it.

The 5-amino-1-phenyl-4-nitropyrazoles obtainable with the aid of the process according to the invention are known herbicides (cf., for example, EP-A 154,155 or EP-A 224,831).

PREPARATION EXAMPLES

Example 1

(a)

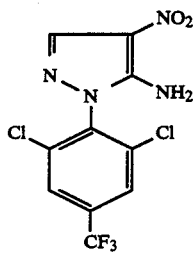

12.3 g (0.14 mole) of an approximately 50% strength aqueous dimethylamine solution are added at 0° C. to 5° C. to 11.5 g (0.07 mole) of 3-chloro-4-nitro-isothiazole in 50 ml of ethanol, the mixture is stirred at room temperature for 1 hour, 12.25 g (0.05 mole) of 2,6-dichloro-4-trifluoromethylphenylhydrazine and 10 ml of 30% strength hydrochloric acid are then added and the mixture is refluxed for 3 hours. The reaction mixture is cooled and filtered, the filtrate is evaporated in vacuo, the residue is stirred with 100 ml of water, and the precipitate thus formed is filtered off with suction, washed with water and dried.

15.6 g (91% of theory) of 5-amino-1-(2,6-dichloro-4-trifluoromethylphenyl)-4-nitropyrazole of melting point 190° C. are obtained.

Example 1

(b)

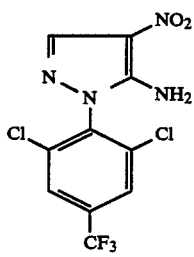

22.6 g (0.22 mole) of an approximately 30% strength aqueous methylamine solution are added at 0° C. to 5° C. to 16.5 g (0.1 mole) of 3-chloro-4-nitro-isothiazole in 200 ml of ethanol, the mixture is stirred at room temperature for 1 hour, 17.2 g (0.07 mole) of 2,6-dichloro-4-trifluoromethylphenylhydrazine and 10 ml of 30% strength hydrochloric acid are then added and the mixture is refluxed for 3 hours. The reaction mixture is cooled and filtered, the filtrate is evaporated in vacuo, the residue is stirred with 100 ml of water, the precipitate thus formed is filtered off with suction, washed with water and dried.

21.5 g (90% of theory) of 5-amino-1-(2,6-dichloro-4-trifluoromethylphenyl)-4-nitropyrazole of melting point 190° C. are obtained.

The following are obtained in a corresponding manner:

Example 2

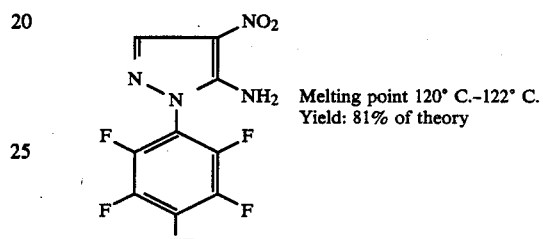

Melting point 120° C.-122° C.
Yield: 81% of theory

Example 3

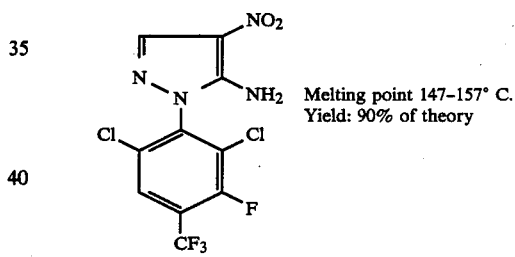

Melting point 147-157° C.
Yield: 90% of theory

It will be appreciated that the instant specification claims are set forth by way of illustration and not limitation, and that various modifications and changes may made without departing from the spirit and scope of the present invention.

What is claimed is:

1. A process for the preparation of a 5-amino-1-phenyl-4-nitropyrazole of the formula

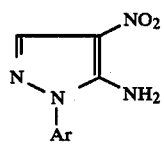 (I)

in which

Ar is optionally substituted phenyl, which comprises reacting an arylhydrazine of the formula Ar—NH—NH$_2$ (II)

with 3-chloro-4-nitro-isothiazole of the formula

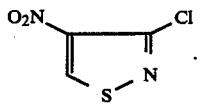

2. A process according to claim 1, wherein the reaction is carried out at a temperature from about −30° C. to +150° C.

3. A process according to claim 1, wherein about 1 to 1.5 moles of 3-chloro-4-nitro-isothiazole are employed per mole of arylhydrazine.

4. A process according to claim 1, wherein about 1 to 1.3 moles of 3-chloro-4-nitro-isothiazole are employed per mole of arylhydrazine.

5. A process according to claim 1, wherein the reaction is effected in the presence of an auxiliary base.

6. A process according to claim 5, wherein the auxiliary base is an amine of the formula

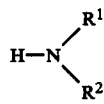

in which $R^1$ and $R^2$ each independently is hydrogen, alkyl, cycloalkyl, or in each case optionally substituted aralkyl, aryl or heteroaryl, or together with the nitrogen atom to which they are bonded form an optionally substituted heterocyclic ring.

7. A process according to claim 6, in which $R^1$ and $R^2$ each independently is hydrogen, straight-chain or branched alkyl having 1 to 4 carbon atoms, cycloalkyl having 3 to 7 carbon atoms, or phenyl or benzyl, each optionally monosubstituted, disubstituted or trisubstituted by identical or different substituents, from the group consisting of fluorine, chlorine, bromine, cyano, nitro, methyl, ethyl, n- or i-propyl, n-, i-, s- or t-butyl, methoxy, ethoxy, n- or i-propoxy, methylthio, trifluoromethyl, trifluoromethoxy, trifluoromethylthio, methoxycarbonyl or ethoxycarbonyl, or $R^1$ and $R^2$ together with the nitrogen atom to which they are bonded form for a five- or six-membered saturated heterocyclic ring which can contain 1 to 3 further identical or different hetero atoms.

8. A process according to claim 5, wherein the auxiliary base is an alkali metal hydroxide, alkaline-earth metal hydroxide, alkali metal carbonates, alkali metal hydrogen carbonates, alkali metal acetate or tertiary amine.

9. A process according to claim 1, wherein the reaction is carried out in the presence of an acid reaction auxiliary.

10. A process according to claim 9, wherein the acid reaction auxiliary is an inorganic mineral acid, aliphatic or aromatic carboxylic acid, aliphatic or aromatic sulphonic acid, Lewis acid or acid ion exchanger.

* * * * *